United States Patent [19]

Stackman et al.

[11] 3,943,199

[45] Mar. 9, 1976

[54] BROMINATED AROMATIC POLYPHOSPHATE COPOLYMERS

[75] Inventors: Robert W. Stackman, Morristown; Frank M. Berardinelli, Millington, both of N.J.

[73] Assignee: Celanese Corporation, New York, N.Y.

[22] Filed: July 23, 1974

[21] Appl. No.: 490,996

Related U.S. Application Data

[62] Division of Ser. No. 432,372, Jan. 10, 1974, Pat. No. 3,883,471.

[52] U.S. Cl. .............................................. 260/930
[51] Int. Cl.² ......................................... C07F 9/12
[58] Field of Search ............................ 260/930, 2 P

[56] References Cited
UNITED STATES PATENTS 3,354,240   11/1967   Pochowicz ..................... 260/930 X
3,706,821   12/1972   Anderson et al. .............. 260/930 X

*Primary Examiner*—Richard L. Raymond

[57] ABSTRACT

An improved flame retardant molding composition of polypropylene terephthalate or polybutylene terephthalate is provided. The composition includes in intimate admixture an oxide of antimony and a specific brominated aromatic polyphosphate copolymer which has been found to be highly compatible with the other components. In a preferred embodiment the molding composition additionally includes a reinforcing agent (e.g. a glass fiber reinforcing agent). Unlike the flame retardant molding compositions of the prior art, the components of the same tend to be non-exuding during utilization of a resulting three-dimensional shaped article at elevated temperatures (e.g. after 66 hours at 175°C.) and thereby render the same suitable for attractive utilization in an even wider range of applications.

2 Claims, No Drawings

BROMINATED AROMATIC POLYPHOSPHATE COPOLYMERS

This is a division of application Ser. No. 432,372, filed Jan. 10, 1974, now U.S. Pat. No. 3,883,471.

BACKGROUND OF THE INVENTION

Polypropylene terephthalate and polybutylene terephthalate molding resins, along with polyethylene terephthalate were first disclosed in U.S. Pat. No. 2,465,319 to Whinfield and Dickson.

The utilization of polypropylene terephthalate and polybutylene terephthalate as molding resins is becoming increasingly accepted in recent years. For example, polypropylene terephthalate and polybutylene terephthalate can be molded and processed at lower temperatures, have a shorter cycle time in the mold and do not require, as does polyethylene terephthalate, the presence of either a nucleating agent or an internal mold release agent. Reinforced polypropylene terephthalate and polybutylene terephthalate molding resins suprisingly have been found to be superior to similarly reinforced polyethylene terephthalate in many important processing and performance characteristics. Furthermore, reinforced polypropylene terephthalate and polybutylene terephthalate molding resins have correspondingly higher tensile strength, lower water absorption and better creep (flexural) properties than does similarly reinforced polyethylene terephthalate. See commonly assigned U.S. Ser. No. 854,259, filed Aug. 29, 1969, of Daniel D. Zimmerman and Robert B. Isaacson, now abandoned in favor of U.S. Ser. No. 373,834, filed June 26, 1973 and now U.S. Pat. No. 3,814,725.

Polypropylene terephthalate and polybutylene terephthalate, just as polyethylene terephthalate, however inherently possess the disadvantage of being flammable, and when burning tend to drip a significant quantity of flaming droplets. Such disadvantage limits their use to those applications where this shortcoming can be tolerated.

Various proposals have heretofore been made for reducing the burning characteristics of polypropylene terephthalate and polybutylene terephthalate. See, commonly assigned U.S. Ser. No. 46,823 to John S. Gall, now abandoned, commonly assigned U.S. Pat. No. 3,751,396 to John S. Gall, and U.S. Pat. No. 3,624,024 to John R. Caldwell and Marvin A. McCall. It has been disclosed, inter alia, to incorporate within the polypropylene terephthalate, or polybutylene terephthalate an organic flame retardant additive such as decabromodiphenyl oxide, tetrabromophthalac anhydride, tetrabromobisphenol A diacetate, 3, 4, 5, 6-tetrabromo-N-methylphthalimide, etc. Antimony trioxide may also be included. It has been observed, however, that the polypropylene terephthalate and polybutylene terephthalate molding compositions of the prior art which incorporate the various flame retardant additives heretofore proposed tend to possess properties which interfere with the appearance of molded articles formed from the same in some end use applications. For instance, the flame retardant additives heretofore proposed tend to separate from the polymeric matrix and to exude from the same at elevated temperatures. The additive may become visually apparent upon the surface of the molded article as a fine powder.

Also, as discussed in U.S. Pat. No. 3,751,396 polypropylene terephthalate and polybutylene terephthalate molding compositions containing flame retardant additives of the prior art may have a tendency drip flaming particles when subjected to flame. An approach to overcome this deficiency has required the additional incorporation of a supplemental reinforcing agent, such as asbestos, having a length to diameter ratio greater than 50:1.

In our commonly assigned U.S. Ser. No. 432,275, filed Jan. 10, 1974 and entitled "Molding Composition Suitable for Forming Improved Flame Retardant Three-Dimensional Shaped Articles,", now abandoned, is claimed a polypropylene terephthalate or polybutylene terephthalate molding composition which includes a certain brominated aromatic polyphosphate homopolymer, a reinforcing agent, and an oxide of antimony.

It is an object of the present invention to provide a polypropylene terephthalate or polybutylene terephthalate molding composition suitable for forming improved flame retardant three-dimensional shaped articles.

It is an object of the present invention to provide a flame retardant polypropylene terephthalate or polybutylene terephthalate molding composition which includes in intimate admixture therewith a flame retardant additive which is non-exuding from the resulting three-dimensional molded article even at elevated temperatures.

It is an object of the present invention to provide an improved flame retardant polyproylene terephthalate or polybutylene terephthalate molding composition which is capable of forming a molded three-dimensional shaped article which is non-dripping when subjected to flame even in the absence of asbestos.

It is an object of the present invention to provide an improved self-extinguishing polypropylene terephthalate or polybutylene terephthalate molding composition which is capable of forming a three-dimensional shaped article which passes the UL-94 Flammability Test.

It is another object of the present invention to provide an improved flame retardant molding composition which is capable of forming three-dimensional shaped articles exhibiting highly satisfactory strength properties.

These and other objects as well as the scope, nature, and utilization of claimed invention will be apparent from the following detailed description and appended claims.

SUMMARY OF THE INVENTION

It has been found that in a molding composition having flame retardant properties when molded into three-dimensional articles comprising an intimate blend of a. a polyalkylene terephthalate selected from the group consisting of polypropylene terephthalate and polybutylene terephthalate having an inherent viscosity of about 0.2 to about 1.4 deciliters per gram,
b. an organic flame retardant additive, and
c. an oxide of antimony;

improved results are achieved by providing as said organic flame retardant additive a brominated aromatic polyphosphate copolymer of the formula

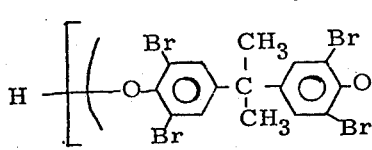

where $x =$ about 1 to 3, $y =$ about 1 to 3 and $n =$ about 2 to 30 with said polymeric brominated aromatic phosphate exhibiting no propensity to exude from said intimate blend during utilization of a three-dimensional article molded therefrom at an elevated temperature of 175°C. for 66 hours.

DESCRIPTION OF PREFERRED EMBODIMENTS

The primary component of the molding composition is a polyalkylene terephthalate polymer selected from the group consisting of polypropylene terephthalate and polybutylene terephthalate. These polymers which are of the general type described in U.S. Pat. No. 2,465,319 to Whinfield and Dickson, can be produced from the reaction product of a dibasic acid, such as terephthalic acid or a dialkyl ester of terephthalic acid (especially dimethyl terephthalate) and diols having 3 to 4 carbon atoms. Suitable diols include 1, 3-propanediol, 1, 4-butanediol, 1, 3-butanediol, 1, 2-propanediol, 1, 2-butanediol, 2, 3-butanediol, and the like.

In the production of the polyproylene terephthalate or polybutylene terephthalate, the appropriate bis(hydroxyalkyl) terephthalate is produced as the intermediate. The bis(hydroxyalkyl) terephthalate can be prepared by reacting the dialkyl ester of terephthalic acid in which the alkyl radicals can contain from 1 to 7 carbon atoms with about two molecular proportions of the diols described above. It is preferred to use higher proportions of the diol, i.e. in excess of 1.5 moles of the diol per mole of the terephthalate derivative, since by using such proportions, the initial transesterification is caused to take place more rapidly and completely.

The esterification reaction is conducted under conditions of elevated temperatures and atmospheric, subatmospheric, or superatmospheric pressure. Normally, the desired temperatures for the polyalkylene terephthalate forming reaction can range from about the boiling temperature of the reaction mixture to as high as 275°C. if desired.

It is recommended that the polypropylene terephthalate or polybutylene terephthalate utilized in the present composition have an inherent viscosity of about 0.2 to 1.4 deciliters per gram, and most preferably an inherent viscosity of about 0.4 to 1.2 deciliters per gram. The inherent viscosity of a given polyalkylene terephthalate sample may be determined at a concentration of 0.1 percent by weight in solvent which is a mixture of 10 parts by weight phenol and 7 parts by weight trichlorophenol.

The flame retardant additive utilized in the improved molding composition of the present invention is polymeric in nature and is of considerably higher molecular weight than the non-polymerized organic flame retardant additives heretofore proposed for incorporation in polypropylene terephthalate and polybutylene terephthalate molding compositions intended for use in the production of three-dimensional shaped articles. More specifically, the organic flame retardant additive is brominated aromatic polyphosphate copolymer (i.e. a brominated aromatic polyester-polyphosphate copolymer) of the formula:

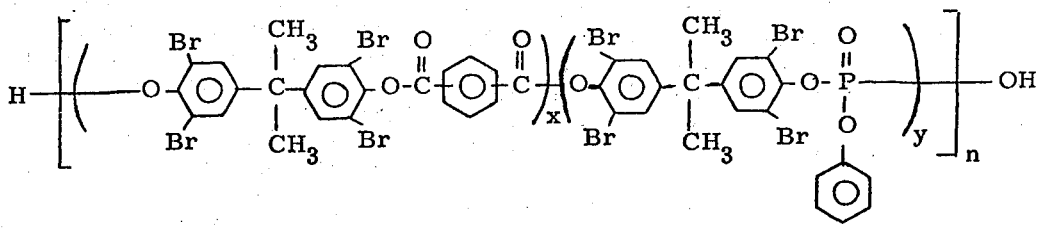

where $x =$ about 1 to 3, $y =$ about 1 to 3, and $n =$ about 2 to 30, and most preferably where $x =$ about 1, $y =$ about 1, and $n =$ about 5 to 15. The additive can be described as poly(2,2-isopropylidene bis p,p'-2,5dibromophenyl phthalate-co phenyl phosphate).

The brominated aromatic polyphosphate copolymer additive may be formed by any one of a variety of polymerization routes with or without the presence of a solvent.

A preferred synthesis route is carried out in the presence of a solvent (e.g. methylene chloride) and a triethylamine acid acceptor. The reactants may be tetrabromobisphenol A, a phthalyl dichloride (i.e. orthophthalyl dichloride, metaphthalyldichloride, or paraphthalyl dichloride, or mixtures thereof), and phenyldichlorophosphate. The hydrogen chloride by-product reacts with the triethylamine to form triethylamine hydrochloride. The relative molar quantities of phthalyl dichloride and phenyldichlorophosphate may be varied within the range of about 1 to 3 moles of phthalyl dichloride per 1 to 3 moles of phenyldichlorophosphate. A substantially stoichiometric quantity of tetrabromobisphenol A is provided to react with the phthalyl dichloride and phenyldichlorophosphate reactants. In the preferred embodiment substantially equal molar quantities of phthalyl dichloride and phenyldichlorophosphate are reacted with an appropriate quantity of tetrabromobisphenol A. The reaction generally maay be illustrated by the following representative equation wherein the phthalydichloride is meta-phthalydichloride (i.e. isophthaloyl chloride):

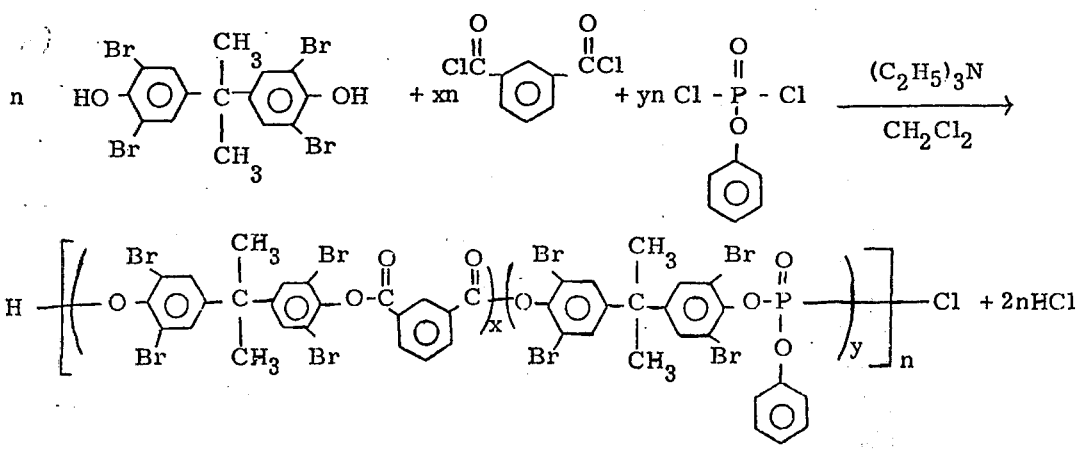

During the synthesis the desired quantities of the reactants may be introduced into a reaction zone at atmospheric pressure provided with a central agitator. The relative quantity of methylene chloride solvent commonly is about 3 to 8 times that of the reactants on a weight basis. The relative quantity of triethylamine introduced commonly is about 20 to 30 percent by weight based upon the weight of the reactants. The contents of the reaction zone may be raised from room temperature to a maximum temperature of about 40 to 60°C. over a period of 15 minutes where they are maintained for about 30 to 90 minutes. The reaction mixture while at a temperature of about 30°C. may be washed with water to remove the triethylamine hydrochloride, and the product recovered by evaporation of the washed methylene chloride solution or by precipitation in a non-solvent. Upon washing the chloride salt is hydrolyzed to yield a hydroxyl end group upon the brominated aromatic polyphosphate as previously illustrated. The solid product formed by this route has a white to pale cream color, commonly exhibits a melting temperature of about 240°C., and an inherent viscosity of about 0.1 to 0.6 as determined at a 0.1 percent by weight concentration in methylene chloride.

Other routes whereby the brominated aromatic polyphosphate copolymer may be formed include the interfacial condensation of tetrabromobisphenol A with a phthalyl dichloride (i.e. ortho-phthalyl dichloride, meta-phthalyldichloride, or para-phthalyl dichloride, or mixtures thereof) and phenyldichlorophosphate in the presence of NaOH, etc.

The third essential component of the molding composition in accordance with the present invention is an oxide of antimony, e.g. antimony trioxide ($Sb_2O_3$) or antimony pentoxide ($Sb_2O_5$). This component preferably is provided as a finely divided powder and serves in conjunction with the brominated aromatic polyphosphate copolymer heretofore described to impart a high degree of flame retardancy to the resulting molding composition. The antimony trioxide component is sometimes identified as antimony white, or antimony oxide. The antimony pentoxide component is sometimes identified as antimonic anhydride, antimonic acid or stibic anhydride.

The brominated aromatic polyphosphate copolymer additive heretofore identified preferably is provided in the molding composition in a concentration of about 15 to 30 percent by weight based upon the weight of the polyalkylene terephthalate component, i.e. the polypropylene terephthalate or polybutylene terephthalate. In a particularly preferred embodiment of the composition the brominated aromatic polyphosphate copolymer additive is provided in the molding composition in a concentration of about 17 to 25 percent by weight based upon the weight of the polyalkylene terephthalate component. If the additive is present in a concentration much below about 15 percent by weight, then samples tend to burn continuously when a molded article formed from the composition is subjected to flame. If the additive is present in a concentration much above about 30 percent by weight, then the strength properties of a molded article formed from the composition may be adversely influenced.

The oxide of antimony component is preferably provided in the molding composition in a concentration of about 4 to 8 percent by weight based upon the weight of the polyalxylene terephthalate component. In a particularly preferred embodiment of the composition the oxide of antimony is provided in the molding composition in a concentration of abut 4.5 to 7.5 percent by weight based upon the weight of the polyalkylene terephthalate component. If the oxide of antimony is present in a concentration much below about 4 percent by weight, then samples tend to burn continuously when a molded article formed from the composition is subjected to flame. If the oxide of antimony is present in a concentration much above about 8 percent by weight, then the strength properties of a molded article formed from the composition may be adversely influenced.

A reinforcing agent optionally may be included in the improved molding composition of the present invention. For instance, a reinforcing agent may be present in concentration of about 2 to about 60 percent by weight, based upon the total weight of the composition (e.g. in a concentration of about 5 to about 40 percent by weight or 20 to 40 percent by weight). Representative reinforcing agents include glass fibers, asbestos fibers, cellulosic fibers, cotton fibers, synthetic polymeric fibers, inorganic or metallic powders, acicular calcium metasilicate (see U.S. Pat. No. 3,764,576), and the like. The particularly preferred reinforcing agent is glass fiber, which may be chopped in lengths of about 1/16 inch or shorter to ¼ inch as added or longer. The preferred length for the glass fiber reinforced is about ⅛ to 3/16 inch. Minor quantities of other additives for appearance and property improvement additionally may be incorporated in the molding composition, such as colorants, plasticizers, stabilizers, hardeners, coupling agents, and the like. As discussed hereafter it is not essential that asbestos fiber be included in the composition to obtain a glass filled molding composition exhibiting non-dripping characteristics when molded into thin sections (see U.S. Pat. No. 3,751,396).

It has been found that a preferred fiber reinforced molding composition in accordance with the present invention comprises an intimate blend of about a. 40 to 70 percent by weight (e.g. 53 percent) polybutylene terephthalate having an inherent viscosity of about 0.4 to 1.2 deciliters per gram (e.g. 0.75)
b. 10 to 15 percent by weight (e.g. 12 percent) brominated aromatic phosphate of the formula

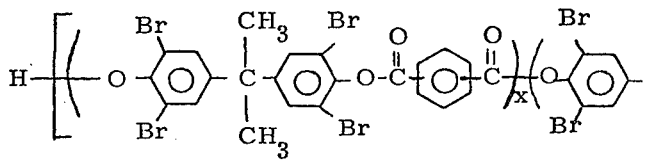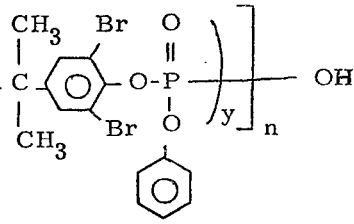

where $x =$ about 1 to 3, $y =$ about 1 to 3, and $n =$ about 2 to 30,
c. about 3 to 5 percent by weight (e.g. 4 percent of an oxide of antimony and,
d. about 20 to 40 percent by weight (e.g. 31 percent) of glass fiber reinforcing agent, with the composition when molded (1) being self-extinguishing and non-dripping when subjected to the UL-94 Flammability Test, and (2) showing no propensity for any component thereof to exude from the same at an elevated temperature of 175°C. for 66 hours.

The components of the improved molding composition may be admixed to form the desired intimate blend by either dry blending or melt blending. The blending may be carried out through the use of extruders, heated rolls, or other types of mixers, as will be apparent to those skilled in the art. For instance, the components may be tumble blended and melt extruded at 240° to 270°C. for pelletizing.

The molding composition of the present invention may be readily molded to form three-dimensional shaped article using conventional molding techniques commonly utilized for polypropylene terephthalate and polybutylene terephthalate. Either compression or injection molding procedures may be utilized. It is preferable that the molding technique utilized not result in any substantial fracture of the reinforcing agent.

The composition of the present invention when molded into a three-dimensional shaped article is particularly suited for use in applications where a high degree of flame retardant properties is essential and the usual exudation at elevated temperatures of the flame retardant additives heretofore incorporated in polypropylene terephthalate and polybutylene terephthalate is considered undesirable. For instance, the composition of the present invention is particularly suited for use in high temperature electrical applications, distributor caps, terminal blocks, miscellaneous automotive under-the-hood applications, etc. When a reinforcing agent (e.g. glass fiber) is present, then the three-dimensional molded articles are better able to serve in high temperature environments e.g. at 140° to 200°C., because of the stiffening role served by the reinforcing agent.

When no reinforcing agent is present, the resulting three-dimensional molded articles may be employed to advantage in applications where a more flexible article is desirable in environments generally not exceeding about 50° to 60°C. when under a load. However, in the absence of a reinforcing agent, e.g. glass fibers, the resulting three-dimensional shaped articles will have a tendency to drip when subjected to flame.

It has been found that the polyalkylene terephthalate, the brominated aromatic polyphosphate copolymer and the oxide of antimony components of the molding composition surprisingly exhibit a high degree of compatibility and may be compounded with ease. No exudation of components from a shaped article formed from the same is observed at ambient conditions. Reinforced molded articles even may be utilized for prolonged periods at elevated temperatures, e.g. up to about 175°C., or more, without exudation. A simple test for the presence or absence of exudation at elevated temperatures may be simply conducted by heating a reinforced molded article in an air atmosphere at 175°C. for 66 hours, and the article subsequently observed. The molded articles formed from the composition additionally exhibit satisfactory strength properties.

The superiority of the resulting glass fiber reinforced three-dimensional shaped articles may be confirmed via the standard UL-94 Flammability Test as mentioned. For instance, a bar of 4 inches × ½ inch × 1/16 inch may be formed by injection molding. The molded article is vertically mounted in a clamp, and a cotton pad is placed 12 inches below the bottom edge of the article. A ¾ inch blue flame from a natural gas Bunsen burner is applied to the lower edge of the article for 10 seconds, the burner is removed and flame-out time is determined, the flame immediately is reapplied for 10 seconds, and the flame is removed and flame-out time is again determined. In order for the article to pass this test it must: (a) not have any article burn for more than 10 seconds after each application of the flame, (b) not have a total flaming time exceeding 50 seconds for a set of 5 articles, and have no molten drippings ignite the cotton pad.

For the purposes of the present description a given molded article is considered to be "non-dripping" when in accordance with the above test no burning droplets are observed when the flame is removed. For the purposes of the present description a given molded article is considered to be "self-extinguishing" when in accordance with the above test it does not burn longer than 10 seconds when the flame is removed. When a reinforcing agent is absent in the composition, molten drops may leave the article when subjected to the flame; however, the cotton pad is normally not ignited. If a reinforcing agent is present in the composition when subjected to the flame, commonly no molten drops leave the same when subjected to flame.

The following examples are given as specific illustrations of the claimed invention. It should be understood, however, that the invention is not limited to the specific details set forth in the examples.

In each example the polybutylene terephthalate component is formed via the procedure described in U.S. Pat. No. 2,465,319 to Whinfield and Dickson. More specifically, 4 parts by weight dimethylterephthalate and 3 parts by weight 1,4-butanediol are mixed together in the presence of 0.0004 part titanium/silicon catalyst. The polybutylene terephthalate has an inherent viscosity of 0.7 deciliters per gram determined at a concentration of 0.1 percent by weight in a solvent which is a mixture of 10 parts by weight phenol and 7 parts by weight trichlorophenol.

In each example the brominated aromatic polyphosphate copolymer additive of the formula previously illustrated (when $x = 1$, $y = 1$, and $n =$ about 15) is formed via the reaction of tetrabromobisphenol A with equal molar quantities of meta-phthalyl dichloride and phenyldichlorophosphate in the presence of a methylene chloride solvent and a triethylamine acid acceptor. More specifically, 566 parts by weight tetrabromobisphenol A, 103 parts by weight phthalyl chloride, 105.5 parts by weight phenyldichlorophosphate, 5000 parts by weight methylene chloride, 204 parts by weight triethylamine are provided in a reaction zone. The tetrabromobisphenol A, methylene chloride, and triethylamine are changed to the reaction zone which is provided with a stirrer, reflux condenser, and addition port. The meta-phthalyl dichloride and phenyldichlorophosphate gradually are added in methylene chloride solution over a one hour period and the temperature raised to 50°C. over a period of 15 minutes, stirred for 90 minutes at 50°C., washed three times with a 3 percent by weight hydrochloric acid solution, washed three times with water, and the product recovered by precipitation in rapidly stirred methanol. The product is subsequently dried in a forced air oven at 60°C. for 12 hours. The resulting brominated aromatic polyphosphate copolymer exhibits a melting point of 230°–240°C., and an inherent viscosity of 0.3 as determined at a 0.1 percent concentration in methylene chloride.

EXAMPLE I

Three dimensional shaped articles are formed comprising 53 percent by weight polybutylene terephthalate, 12.4 percent by weight of the brominated aromatic polyphosphate copolymer, 3.6 percent by weight antimony trioxide, and 31 percent by weight ⅛ inch glass fiber. Initially the components are formed into an intimate blend by tumble blending the components and passing the resulting blend through an extruder at 250°to 260°C. for melt blending and pelletizing. The articles are injection molded into bars of 4 inches × ½ inch × 1/16 inch using a melt temperature of 255°C., a mold temperature of 65°C., and an injection pressure of about 8500 psi. The components of the molded article are found to be non-exuding from the resulting three-dimensional shaped articles after 66 hours at 175°C. The three-dimensional molded articles have highly satisfactory strength properties, are self-extinguishing and pass the UL-94 Flammability Test.

For comparative purposes both the brominated aromatic polyphosphate copolymer and the antimony trioxide components are omitted from the blend. The resulting molded articles burn vigorously until totally consumed and drip burning droplets which ignite the cotton pad in the UL-94 Flammability Test.

For comparative purposes only the brominated aromatic polyphosphate copolymer is omitted from the blend. The resulting molded articles burn vigorously until totally consumed and drip burning droplets which ignite the cotton pad in the UL-94 Flammability Test.

For comparative purposes only the antimony trioxide component is omitted from the blend. The resulting molded articles burn vigorously until totally consumed and drip burning droplets which ignite the cotton pad in the UL-94 Flammability Test.

For comparative purposes molded control articles are formed utilizing representative flame retardant technology of the prior art. The molded articles comprise 57.8 percent by weight polybutylene terephthalate, 4.8 percent by weight decarbromobiphenyl oxide, 4.8 percent by weight antimony trioxide, 30 percent by weight of ⅛ inch glass fiber, and 2.6 percent by weight asbestos fiber of 5–25 microns. The decabromobiphenyl oxide component of the resulting three-dimensional shaped articles is found substantially to exude onto the surface of the article after 66 hours at 175°C. The molded articles are non-dripping and self-extinguishing and pass the UL-94 Flammability Test. If the asbestos component is omitted from the control then the molded article will drip a substantial quantity of burning droplets, and may fail the UL-94 Flammability Test by igniting the cotton pad.

EXAMPLE II

Example I is repeated with the following exceptions. No reinforcing agent is included. The resulting molded article consists of 74.3 percent by weight polybutylene terephthalate, 20 percent by weight of the brominated aromatic polyphosphate copolymer, and 5.7 percent by weight antimony trioxide. The article passes the UL-94 Flammability Test, but molten drops tend to leave the article when subjected to flame. The cotton pad used in the test normally is not ignited. The components of the supported molded article are non-exuding after 66 hours at 175°C.

For comparative purposes a comparable non-reinforced molded article is formed wherein the organic flame retardant additive is decabromobiphenyl oxide instead of the brominated aromatic polyphosphate copolymer. Exudation is apparent after 66 hours at 175°C.

Substantially similar results are obtained when polypropylene terephthalate is substituted for polybutylene terephthalate and/or antimony pentoxide is substituted for antimony trioxide in Example I and Example II.

Although the invention has been described with preferred embodiments it is understood that variations and modifications may be resorted to as will be apparent to those skilled in the art. Such variations and modifications are to be considered within the purview and scope of the claims appended hereto.

We claim:

1. A brominated aromatic polyphosphate copolymer of the formula

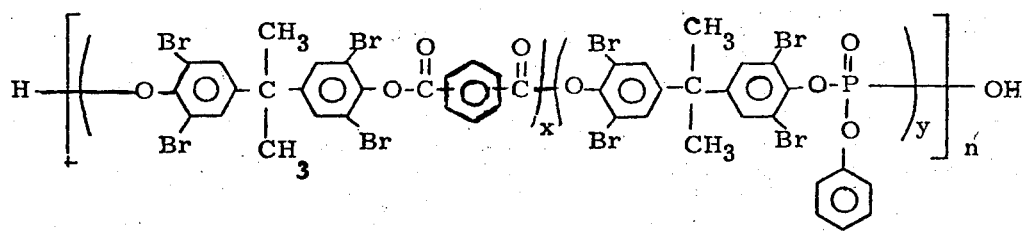
where $x$ = about 1 to 3, $y$ = about 1 to 3, and $n$ = about 2 to 30.
2. A brominated aromatic polyphosphate copolymer in accordance with claim 1 wherein $x$ = about 1, $y$ = about 1, and $n$ = about 5 to 15.
* * * * *